US012059289B2

United States Patent
Rouet et al.

(10) Patent No.: US 12,059,289 B2
(45) Date of Patent: Aug. 13, 2024

(54) METHODS AND SYSTEMS FOR PERFORMING FETAL WEIGHT ESTIMATIONS

(71) Applicant: KONINKLIJKE PHILIPS N.V., Eindhoven (NL)

(72) Inventors: Laurence Rouet, Paris (FR); Caroline Denise Raynaud, Paris (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 787 days.

(21) Appl. No.: 17/259,294

(22) PCT Filed: Jul. 1, 2019

(86) PCT No.: PCT/EP2019/067505
§ 371 (c)(1),
(2) Date: Jan. 11, 2021

(87) PCT Pub. No.: WO2020/011569
PCT Pub. Date: Jan. 16, 2020

(65) Prior Publication Data
US 2021/0298717 A1    Sep. 30, 2021

(30) Foreign Application Priority Data

Jul. 10, 2018  (EP) .................................. 18290075

(51) Int. Cl.
*A61B 8/08*      (2006.01)
*A61B 8/00*      (2006.01)
(Continued)

(52) U.S. Cl.
CPC ............ *A61B 8/0866* (2013.01); *A61B 8/466* (2013.01); *A61B 8/467* (2013.01); *A61B 8/5223* (2013.01);
(Continued)

(58) Field of Classification Search
CPC ....... A61B 8/0866; A61B 8/466; A61B 8/467; A61B 8/5223; A61B 8/483; G06T 7/0014;
(Continued)

(56) References Cited

U.S. PATENT DOCUMENTS 6,375,616 B1 *   4/2002  Soferman ............ A61B 8/0866
                                                       600/443
6,575,907 B1 *   6/2003  Soferman ............ A61B 5/1075
                                                       600/443
(Continued)

FOREIGN PATENT DOCUMENTS

CN           107766874 A      3/2018

OTHER PUBLICATIONS

International Report and Written Opinion for International Application No. PCT/EP2019/067505, filed Jul. 1, 2019, 15 pages.
(Continued)

*Primary Examiner* — Patrick Fernandes
*Assistant Examiner* — Nicholas A Robinson

(57) ABSTRACT

The invention provides a method for estimating the weight of a fetus. A plurality of different three dimensional ultrasound images of an imaging region are acquired, wherein the plurality of different three dimensional ultrasound images comprise: a head image; an abdominal image; and a femur image. Each of the plurality of different three dimensional ultrasound images undergoes segmentation and the fetal weight estimation is performed based on the resulting segmentations.

19 Claims, 6 Drawing Sheets

(51) Int. Cl.
*G06T 7/00* (2017.01)
*G06T 7/11* (2017.01)

(52) U.S. Cl.
CPC .............. *G06T 7/0014* (2013.01); *G06T 7/11* (2017.01); *G06T 2207/10136* (2013.01); *G06T 2207/20084* (2013.01); *G06T 2207/30008* (2013.01); *G06T 2207/30044* (2013.01)

(58) Field of Classification Search
CPC .............. G06T 7/11; G06T 2207/10136; G06T 2207/20084; G06T 2207/30008; G06T 2207/30044; G06T 7/0012; G06T 7/62; G16H 50/30
See application file for complete search history.

(56) References Cited

U.S. PATENT DOCUMENTS

| | | |
|---|---|---|
| 2007/0081705 A1 | 4/2007 | Carneiro et al. |
| 2008/0114243 A1 | 5/2008 | Oonuki |
| 2010/0322495 A1 | 12/2010 | Collet-Billon et al. |
| 2012/0232394 A1* | 9/2012 | Toji ................. A61B 8/5223 600/443 |
| 2016/0058422 A1 | 3/2016 | Lee et al. |
| 2016/0081663 A1 | 3/2016 | Chen et al. |

OTHER PUBLICATIONS

Lee, et al., "Prospective validation of fetal weight estimation using fractional limb volume", Ultrasound Obstet Gynecol., Feb. 2013, 41(2), pp. 198-203.
Scioscia, et al., "Estimation of Birth Weight by Two-Dimensional Ultrasonography", Obstetrics & Gynecology, vol. 111, No. 1, Jan. 2008, pp. 57-65.
Lee, et al., "Fractional limb volume—a soft tissue parameter of fetal body composition: validation, technical considerations and normal ranges during pregnancy", Ultrasound Obstet Gynecol 2009, 33; pp. 427-440.
Lee, et al., "New fetal weight estimation models using fractional limb volume", Ultrasound Obstet Gynecol 2009; 34: pp. 556-565.
Lappen, et al., The systematic error in the estimation of fetal weight and the underestimation of fetal growth pp. 477-483.
Valent, et al., "Accuracy of Sonographically Estimated Fetal Weight Near Delivery in Pregnancies Complicated With Diabetes Mellitus", American Institute of Ultrasound in Medicine 2017, 36: pp. 593-599.
Schild, et al., "Weight estimation by three-dimensional ultrasound imaging in the small fetus", Ultrasound Obstet Gynecol 2008; 32: pp. 168-175.
Cuingnet, et al., "Where is my baby? A fast fetal head auto-alignment in 3D-ultrasound", Biomedical Imaging (ISBI), 2013 IEEE 10th International Symposium on, 768-771.

\* cited by examiner

METHODS AND SYSTEMS FOR PERFORMING FETAL WEIGHT ESTIMATIONS

RELATED APPLICATIONS

This application is the U.S. National Phase application under 35 U.S.C. § 371 of International Application No. PCT/EP2019/067505, filed on Jul. 1, 2019, which claims priority to and the benefit of European Application No. 18290075.3, filed Jul. 10, 2018, which are incorporated by reference in their entireties.

FIELD OF THE INVENTION

This invention relates to the field of ultrasound imaging, and in particular to the field of fetal ultrasound imaging.

BACKGROUND OF THE INVENTION

In current clinical practice, fetal weight is typically estimated using a combination of 2D measurements, extracted from 2D ultrasound images. Some more advanced approaches use fractional limb volume as an additional parameter in fetal weight equations, such as thigh and arm fractional volumes, which enable a reduction of weight estimation error from 8.5% to 6.6%.

Where the fetuses are too small or too large, errors in fetal weight estimation during pregnancy may lead to inadequate care given to the infant during pregnancy or after birth. Depending on the actual weight of the fetus, the balance between relative coefficients used in the current models, will affect the precision of the estimated fetal weight. For example, in the case of fetal weights>3500 g, formulae that depend more on the abdominal circumference and femur length in the calculation provide more accurate predictions of birth weight.

Current equations used for fetal weight estimation are based on statistical regressions and estimations based on population analysis. The number of different equations is very high, which leads to various possible estimates according to the selected model and introduces uncertainty in which model to apply. In addition, the use of fractional limb volume improved precision of the estimated fetal weight; however, only a small amount of information regarding the soft tissues of the fetus is typically used.

There is therefore a need to provide a robust method for performing fetal weight estimation that does not vary significantly across individual cases and does not require significant additional hardware.

Document U.S. Pat. No. 6,375,616 discloses an apparatus for fetal weight determination including an ultrasonic imager operative to image a fetus in utero.

Document US 2012/232394 discloses an ultrasound diagnostic apparatus including a measurement calculation unit, which calculates an estimated weight of a subject.

Document U.S. Pat. No. 6,575,907 discloses an apparatus for measuring the weight of a fetus in utero including an ultrasonic imager providing at least one ultrasonic image.

SUMMARY OF THE INVENTION

The invention is defined by the claims.

According to examples in accordance with an aspect of the invention, there is provided a method for performing fetal weight estimation, the method comprising:

acquiring a plurality of different three dimensional ultrasound images of an imaging region, wherein the plurality of different three dimensional ultrasound images comprise:
   a head image;
   an abdominal image; and
   a femur image;
performing segmentation on each of the plurality of different three dimensional ultrasound images; and
performing fetal weight estimation based on the segmentations of each of the plurality of different three dimensional ultrasound images.

This method acquires several 3D ultrasound images of different areas of a fetus, such as: the head; the abdomen; and the femur, and performs individual image segmentation on each image in order to identify key structures within that image area. For example, the image segmentation performed on the image containing the head of the fetus will be for identifying the skull. Similarly, the image segmentations performed on the abdominal image and the femur image are used to identify the torso and leg, respectively.

Following the separate segmentation of the different images, thereby identifying the key structures within the target volumes, it is possible to generate a complete and accurate estimate of the weight of the fetus.

In an embodiment, the plurality of different three dimensional ultrasound images further comprises a humerus image.

By including a further image containing a relatively large skeletal structure that does not fit into a standard field of view of the fetus, it is possible to further increase the accuracy of the fetal weight estimate.

In an embodiment, the segmentation of the abdominal image comprises:
   generating a model torso image;
   comparing the model torso image to the segmented abdominal image; and
   generating an adjustment factor for the segmented abdominal image based on the comparison.

In this way, it is possible to account for abdominal images which are unable to capture the entire torso of the fetus due to field of view limitations, thereby increasing the accuracy of the fetal weight estimate.

In some embodiments, the segmentation of the femur image comprises:
   detecting a femur by performing extremity classification based on a deep learning network; and
   classifying tissue surrounding the femur.

By detecting the femur and classifying the surrounding tissue, it is possible to accurately segment the fetal tissue from the other tissues which would be included in the femur image, thereby increasing the accuracy of the fetal weight estimation.

In a further embodiment, the classification of tissue surrounding the femur comprises segmenting the femur image based on a dedicated machine learning algorithm.

In this way, it is possible to segment the femur image simply based on a machine learning algorithm, which may be trained to recognize the tissue structures within the femur image, thereby increasing the accuracy of the segmentation of the femur image.

In a further embodiment, the segmentation of the femur image comprises receiving user input.

In this way, it is possible for the user to provide corrections to the segmentation, which may then be used to further train the machine learning algorithm and improve the accuracy of the fetal weight estimation.

In an arrangement, the method further comprises displaying the segmentations of each of the plurality of different three dimensional ultrasound images to a user.

In this way, it is possible for the user to view the segmented images and ensure that the correct areas have been identified. This may help to alert the user to any potential mistakes in the imaging process, thereby increasing the accuracy of the fetal weight estimate.

In a further arrangement, the method further comprises receiving user input based on the displayed segmentations.

The user may provide input to alter the displayed view of the segmented images, allowing them to inspect the image more closely. The user may also provide corrections to errors observed in the image segmentation process, thereby increasing the accuracy of the fetal weight estimate.

In an embodiment, the fetal weight estimation is based on a global homogeneous tissue density.

A global homogeneous tissue density may be used to calculate the fetal weight estimate in a simple manner, which reduces the processing power required to calculate the fetal weight estimate.

In some embodiments, the fetal weight estimation comprises:
  for each segmentation of the plurality of different three dimensional ultrasound images:
    extracting an internal volume of the segmentation;
    analyzing plurality of signal intensities within the internal volume;
    classifying a plurality of tissue types within the internal volume based on the signal intensities; and
    extracting tissue information based on the plurality of tissue types;
  combining the tissue information extracted from each segmentation; and
  estimating the fetal weight based on the tissue information.

For each segmentation of the 3D images, an internal volume may be analyzed. The internal volume may be the entire segmented structure, such as a skull, or it may be a smaller volume within the 3D structure. The signal intensities within the internal volume are then analyzed and classified in order to generate information on the tissues present in the internal volume.

This information may then be combined across all of the image segmentations from the acquired 3D ultrasound images and used to estimate the fetal weight. By analyzing each separate segmented image in this way, it is possible to build a more accurate profile of the fetal composition and so the accuracy of the fetal weight estimate is increased.

In further embodiments, the plurality of tissue types comprises:
  soft tissue;
  bone; and
  fluid.

By identifying these key factors of fetal composition, it is possible to account for the majority of tissue types present within the 3D ultrasound images, thereby increasing the accuracy of the fetal weight estimate.

In further embodiments, the tissue information comprises tissue volumes of the plurality of tissue types within the internal volume.

In this way, the amount of each tissue type present in each segmented image may be used in the fetal weight estimate, thereby increasing the accuracy of the estimate.

In a further embodiment, the estimating of the fetal weight comprises:
  applying an associated tissue density coefficient to each of the plurality of tissue types; and
  calculating a fetal weight estimate based on the tissue volumes and the associated tissue density coefficient of each of the plurality of tissue types.

By taking into account the densities of the various fetal tissues present in the segmented images, the accuracy of the fetal weight estimate is further increased.

According to examples in accordance with an aspect of the invention, there is provided a computer program comprising computer program code means which is adapted, when said computer program is run on a computer, to implement the method above described.

According to examples in accordance with an aspect of the invention, there is provided an ultrasound imaging system comprising:
  an ultrasound probe adapted to acquire three dimensional ultrasound images of an imaging region;
  a display; and
  a processor, wherein the processor is adapted to:
    acquire a plurality of different three dimensional ultrasound images of the imaging region, wherein the plurality of different three dimensional ultrasound images comprise:
      a head image;
      an abdominal image; and
      a femur image;
    perform segmentation on each of the plurality of different three dimensional ultrasound images; and
    perform fetal weight estimation based on the segmentations of each of the plurality of different three dimensional ultrasound images.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
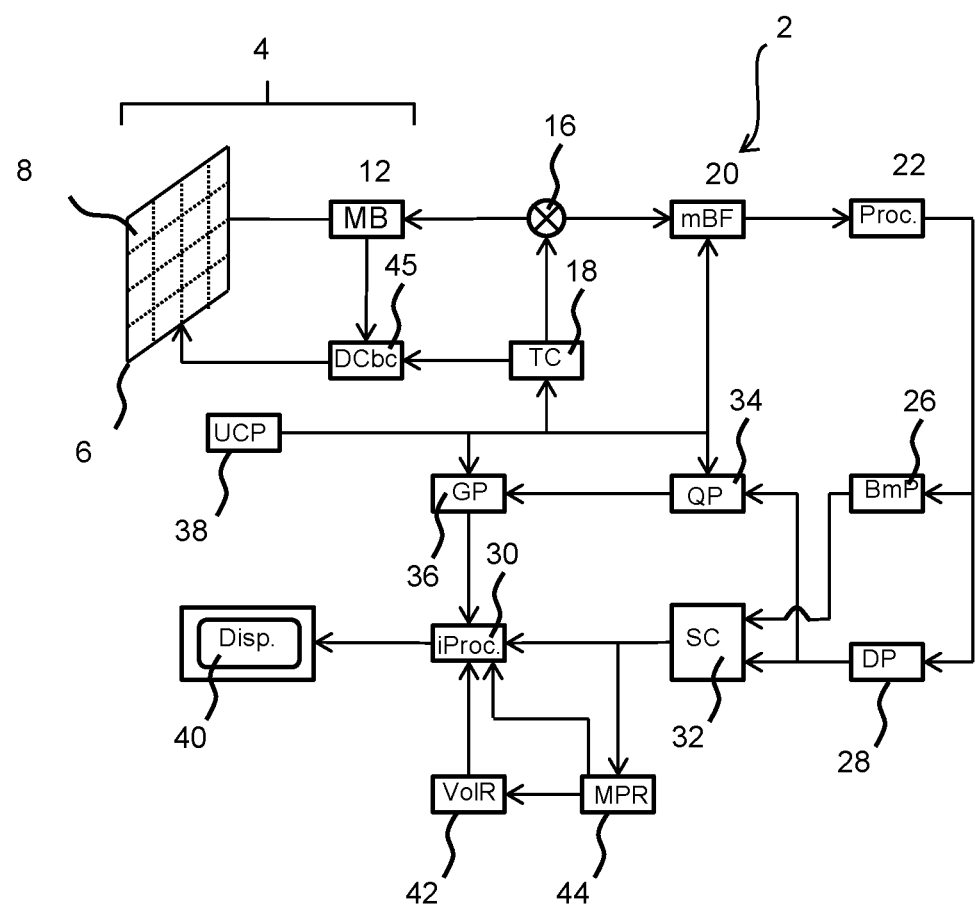
FIG. 1 shows an ultrasound diagnostic imaging system to explain the general operation.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a method for estimating the weight of a fetus. A plurality of different three dimensional ultrasound images of an imaging region are acquired, wherein the plurality of different three dimensional ultrasound images comprise: a head image; an abdominal image; and a femur image. Each of the plurality of different three dimensional ultrasound images undergoes segmentation and the fetal weight estimation is performed based on the resulting segmentations.

The general operation of an exemplary ultrasound system will first be described, with reference to FIG. 1, and with emphasis on the signal processing function of the system since this invention relates to the processing of the signals measured by the transducer array.

The system comprises an array transducer probe 4 which has a transducer array 6 for transmitting ultrasound waves and receiving echo information. The transducer array 6 may comprise CMUT transducers; piezoelectric transducers, formed of materials such as PZT or PVDF; or any other suitable transducer technology. In this example, the transducer array 6 is a two-dimensional array of transducers 8 capable of scanning either a 2D plane or a three dimensional volume of a region of interest. In another example, the transducer array may be a 1D array.

The transducer array 6 is coupled to a microbeamformer 12 which controls reception of signals by the transducer elements. Microbeamformers are capable of at least partial beamforming of the signals received by sub-arrays, generally referred to as "groups" or "patches", of transducers as described in U.S. Pat. No. 5,997,479 (Savord et al.), U.S. Pat. No. 6,013,032 (Savord), and U.S. Pat. No. 6,623,432 (Powers et al.).

It should be noted that the microbeamformer is entirely optional. Further, the system includes a transmit/receive (T/R) switch 16, which the microbeamformer 12 can be coupled to and which switches the array between transmission and reception modes, and protects the main beamformer 20 from high energy transmit signals in the case where a microbeamformer is not used and the transducer array is operated directly by the main system beamformer. The transmission of ultrasound beams from the transducer array 6 is directed by a transducer controller 18 coupled to the microbeamformer by the T/R switch 16 and a main transmission beamformer (not shown), which can receive input from the user's operation of the user interface or control panel 38. The controller 18 can include transmission circuitry arranged to drive the transducer elements of the array 6 (either directly or via a microbeamformer) during the transmission mode.

In a typical line-by-line imaging sequence, the beamforming system within the probe may operate as follows. During transmission, the beamformer (which may be the microbeamformer or the main system beamformer depending upon the implementation) activates the transducer array, or a sub-aperture of the transducer array. The sub-aperture may be a one dimensional line of transducers or a two dimensional patch of transducers within the larger array. In transmit mode, the focusing and steering of the ultrasound beam generated by the array, or a sub-aperture of the array, are controlled as described below.

Upon receiving the backscattered echo signals from the subject, the received signals undergo receive beamforming (as described below), in order to align the received signals, and, in the case where a sub-aperture is being used, the sub-aperture is then shifted, for example by one transducer element. The shifted sub-aperture is then activated and the process repeated until all of the transducer elements of the transducer array have been activated.

For each line (or sub-aperture), the total received signal, used to form an associated line of the final ultrasound image, will be a sum of the voltage signals measured by the transducer elements of the given sub-aperture during the receive period. The resulting line signals, following the beamforming process below, are typically referred to as radio frequency (RF) data. Each line signal (RF data set) generated by the various sub-apertures then undergoes additional processing to generate the lines of the final ultrasound image. The change in amplitude of the line signal with time will contribute to the change in brightness of the ultrasound image with depth, wherein a high amplitude peak will correspond to a bright pixel (or collection of pixels) in the final image. A peak appearing near the beginning of the line signal will represent an echo from a shallow structure, whereas peaks appearing progressively later in the line signal will represent echoes from structures at increasing depths within the subject.

One of the functions controlled by the transducer controller 18 is the direction in which beams are steered and focused. Beams may be steered straight ahead from (orthogonal to) the transducer array, or at different angles for a wider field of view. The steering and focusing of the transmit beam may be controlled as a function of transducer element actuation time.

Two methods can be distinguished in general ultrasound data acquisition: plane wave imaging and "beam steered" imaging. The two methods are distinguished by a presence of the beamforming in the transmission ("beam steered" imaging) and/or reception modes (plane wave imaging and "beam steered" imaging).

Looking first to the focusing function, by activating all of the transducer elements at the same time, the transducer array generates a plane wave that diverges as it travels through the subject. In this case, the beam of ultrasonic waves remains unfocused. By introducing a position dependent time delay to the activation of the transducers, it is possible to cause the wave front of the beam to converge at a desired point, referred to as the focal zone. The focal zone is defined as the point at which the lateral beam width is less than half the transmit beam width. In this way, the lateral resolution of the final ultrasound image is improved.

For example, if the time delay causes the transducer elements to activate in a series, beginning with the outermost elements and finishing at the central element(s) of the transducer array, a focal zone would be formed at a given distance away from the probe, in line with the central element(s). The distance of the focal zone from the probe will vary depending on the time delay between each subsequent round of transducer element activations. After the beam passes the focal zone, it will begin to diverge, forming the far field imaging region. It should be noted that for focal zones located close to the transducer array, the ultrasound beam will diverge quickly in the far field leading to beam width artifacts in the final image. Typically, the near field, located between the transducer array and the focal zone, shows little detail due to the large overlap in ultrasound beams. Thus, varying the location of the focal zone can lead to significant changes in the quality of the final image.

It should be noted that, in transmit mode, only one focus may be defined unless the ultrasound image is divided into multiple focal zones (each of which may have a different transmit focus).

In addition, upon receiving the echo signals from within the subject, it is possible to perform the inverse of the above described process in order to perform receive focusing. In other words, the incoming signals may be received by the transducer elements and subject to an electronic time delay before being passed into the system for signal processing. The simplest example of this is referred to as delay-and-sum beamforming. It is possible to dynamically adjust the receive focusing of the transducer array as a function of time.

Looking now to the function of beam steering, through the correct application of time delays to the transducer elements it is possible to impart a desired angle on the ultrasound beam as it leaves the transducer array. For example, by activating a transducer on a first side of the transducer array followed by the remaining transducers in a sequence ending at the opposite side of the array, the wave front of the beam will be angled toward the second side. The size of the steering angle relative to the normal of the transducer array is dependent on the size of the time delay between subsequent transducer element activations.

Further, it is possible to focus a steered beam, wherein the total time delay applied to each transducer element is a sum of both the focusing and steering time delays. In this case, the transducer array is referred to as a phased array.

In case of the CMUT transducers, which require a DC bias voltage for their activation, the transducer controller 18 can be coupled to control a DC bias control 45 for the transducer array. The DC bias control 45 sets DC bias voltage(s) that are applied to the CMUT transducer elements.

For each transducer element of the transducer array, analog ultrasound signals, typically referred to as channel data, enter the system by way of the reception channel. In the reception channel, partially beamformed signals are produced from the channel data by the microbeamformer 12 and are then passed to a main receive beamformer 20 where the partially beamformed signals from individual patches of transducers are combined into a fully beamformed signal, referred to as radio frequency (RF) data. The beamforming performed at each stage may be carried out as described above, or may include additional functions. For example, the main beamformer 20 may have 128 channels, each of which receives a partially beamformed signal from a patch of dozens or hundreds of transducer elements. In this way, the signals received by thousands of transducers of a transducer array can contribute efficiently to a single beamformed signal.

The beamformed reception signals are coupled to a signal processor 22. The signal processor 22 can process the received echo signals in various ways, such as: band-pass filtering; decimation; I and Q component separation; and harmonic signal separation, which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting noise at higher frequencies from greater depths that is typically devoid of anatomical information.

The beamformers for transmission and for reception are implemented in different hardware and can have different functions. Of course, the receiver beamformer is designed to take into account the characteristics of the transmission beamformer. In FIG. 1 only the receiver beamformers 12, 20 are shown, for simplicity. In the complete system, there will also be a transmission chain with a transmission micro beamformer, and a main transmission beamformer.

The function of the micro beamformer 12 is to provide an initial combination of signals in order to decrease the number of analog signal paths. This is typically performed in the analog domain.

The final beamforming is done in the main beamformer 20 and is typically after digitization.

The transmission and reception channels use the same transducer array 6 which has a fixed frequency band. However, the bandwidth that the transmission pulses occupy can vary depending on the transmission beamforming used. The reception channel can capture the whole transducer bandwidth (which is the classic approach) or, by using bandpass processing, it can extract only the bandwidth that contains the desired information (e.g. the harmonics of the main harmonic).

The RF signals may then be coupled to a B mode (i.e. brightness mode, or 2D imaging mode) processor 26 and a Doppler processor 28. The B mode processor 26 performs amplitude detection on the received ultrasound signal for the imaging of structures in the body, such as organ tissue and blood vessels. In the case of line-by-line imaging, each line (beam) is represented by an associated RF signal, the amplitude of which is used to generate a brightness value to be assigned to a pixel in the B mode image. The exact location of the pixel within the image is determined by the location of the associated amplitude measurement along the RF signal and the line (beam) number of the RF signal. B mode images of such structures may be formed in the harmonic or fundamental image mode, or a combination of both as described in U.S. Pat. No. 6,283,919 (Roundhill et al.) and U.S. Pat. No. 6,458,083 (Jago et al.) The Doppler processor 28 processes temporally distinct signals arising from tissue movement and blood flow for the detection of moving substances, such as the flow of blood cells in the image field. The Doppler processor 28 typically includes a wall filter with parameters set to pass or reject echoes returned from selected types of materials in the body.

The structural and motion signals produced by the B mode and Doppler processors are coupled to a scan converter 32 and a multi-planar reformatter 44. The scan converter 32 arranges the echo signals in the spatial relationship from which they were received in a desired image format. In other words, the scan converter acts to convert the RF data from a cylindrical coordinate system to a Cartesian coordinate system appropriate for displaying an ultrasound image on an image display 40. In the case of B mode imaging, the brightness of pixel at a given coordinate is proportional to the amplitude of the RF signal received from that location. For instance, the scan converter may arrange the echo signal into a two dimensional (2D) sector-shaped format, or a pyramidal three dimensional (3D) image. The scan converter can overlay a B mode structural image with colors corresponding to motion at points in the image field, where the Doppler-estimated velocities to produce a given color. The combined B mode structural image and color Doppler image depicts the motion of tissue and blood flow within the structural image field. The multi-planar reformatter will convert echoes that are received from points in a common plane in a volumetric region of the body into an ultrasound image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.).

The 2D or 3D images are coupled from the scan converter 32, multi-planar reformatter 44, and volume renderer 42 to an image processor 30 for further enhancement, buffering and temporary storage for display on an image display 40. The imaging processor may be adapted to remove certain imaging artifacts from the final ultrasound image, such as: acoustic shadowing, for example caused by a strong attenuator or refraction; posterior enhancement, for example caused by a weak attenuator, reverberation artifacts, for example where highly reflective tissue interfaces are located in close proximity; and so on. In addition, the image processor may be adapted to handle certain speckle reduction functions, in order to improve the contrast of the final ultrasound image.

In addition to being used for imaging, the blood flow values produced by the Doppler processor 28 and tissue structure information produced by the B mode processor 26 are coupled to a quantification processor 34. The quantification processor produces measures of different flow conditions such as the volume rate of blood flow in addition to structural measurements such as the sizes of organs and gestational age. The quantification processor may receive input from the user control panel 38, such as the point in the anatomy of an image where a measurement is to be made.

Output data from the quantification processor is coupled to a graphics processor 36 for the reproduction of measurement graphics and values with the image on the display 40, and for audio output from the display device 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name. The user interface is also coupled to the transmit controller 18 to control the generation of ultrasound signals from the transducer array 6 and hence the images produced by the transducer array and the ultrasound system. The transmit control function of the controller 18 is only one of the functions performed. The controller 18 also takes account of the mode of operation (given by the user) and the corresponding required transmitter configuration and band-pass configuration in the receiver analog to digital converter. The controller 18 can be a state machine with fixed states.

The user interface is also coupled to the multi-planar reformatter 44 for selection and control of the planes of multiple multi-planar reformatted (MPR) images which may be used to perform quantified measures in the image field of the MPR images.

Figure 2:
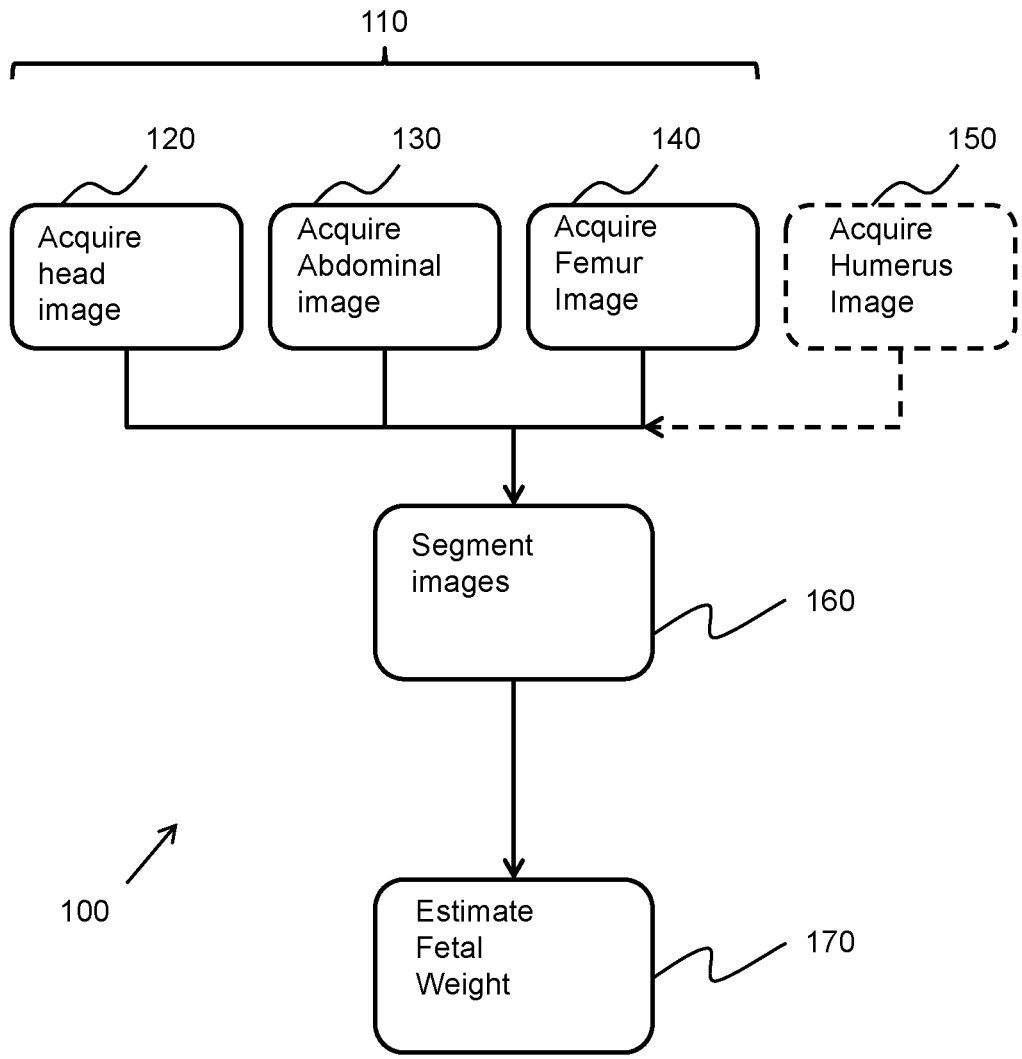
FIG. 2 shows a method of the invention.

FIG. 2 shows a method 100 for performing fetal weight estimation.

The method begins by acquiring a plurality of different three dimensional ultrasound images 110 of a desired imaging region of a fetus.

The plurality of different three dimensional ultrasound images may be three dimensional ultrasound images that have been separately acquired. For example, the plurality of different three dimensional ultrasound images may each be acquired: at a different point in time; from a different acquisition location; using different imaging parameters; and the like, so as to optimize the visualization and/or coverage of an anatomical structure in the respective images.

In other words, each of the plurality of different three dimensional ultrasound images may correspond to a different ultrasound acquisition. An enhanced visualization and/or coverage of the anatomical structures will translate into improved segmentations, which in turn will lead to a more accurate weight estimation.

In step 120, a head image is acquired that includes the head of the fetus. The head image may be captured with optimal coverage, containing the entire skull and base of the neck of the fetus.

In step 130, an abdominal image is acquired that includes the torso of the fetus.

Due to restrictions of the field of view of some ultrasonic probes, it may not be possible to capture the entire torso of the fetus, in which case the abdominal image will include a partial torso of the fetus. In this case, the acquisition settings may be selected in order to obtain the largest field of view possible.

In step 140, a femur image is acquired that includes a leg of the fetus.

During the acquisition of the femur image, the field of view may be centered on the femur and adapted to capture the surrounding soft thigh tissue in addition to the bone.

In step 150, a humerus image may be acquired that includes an arm of the fetus.

In a similar manner to the acquisition of the femur image, the field of view may be centered on the humerus during the acquisition process and adapted to capture the surround soft upper arm tissue.

In step 160, each of the acquired plurality of different three dimensional ultrasound images undergoes segmentation.

The segmentation of the head image may be used to identify the skull of the fetus, as this is where the majority of the mass of the head is located. The segmentation of the head image may be performed as described in R Cuingnet et al. Where is my baby? A fast fetal head auto-alignment in 3D-ultrasound, Biomedical Imaging (ISBI), 2013 IEEE 10th International Symposium on, 768-771.

In the case where the entire torso may be contained within the field of view of the abdominal image, the segmentation of the torso may be performed by known segmentation methods, such as thresholding.

For example, the segmentation of an abdominal image may be carried out as follows.

The first step in the segmentation may be to detect the spine of the fetus within the abdominal image and derive a first reference (orientation) axis, herein noted as the n-axis.

The spine may be automatically detected in a 3D ultrasound abdominal image by combining a morphological filter which detects elongated bright structures and a deep learning (DL) based vertebrae detector, in order to take advantage of the strengths of both methods.

A morphological filter may be used for each voxel x in the abdominal image volume in a given spherical neighborhood, to compare the intensity of the voxels along a direction u with the intensity of the other voxels. The filter responses are computed for various neighborhood radii and orientations u and combined to obtain a global response. The global responses of neighboring voxels are aggregated to define connected components which correspond to the best filter responses.

Although some of the responses are accurately positioned on the spine using this approach, others may also be present which are outliers, that may for example be located on ribs or other elongated structures such as long bones.

The deep learning-based vertebrae detector is a 2D fully convolutional network whose input is made of 2D slices, extracted orthogonally to an image-based z-axis. The volume slicing produces a large amount of data with similar features, which is appropriate for deep learning methods. The network output is a down sampled probability map, with values closer to 1 where the spine might be located. A 3D deep learning-based vertebrae detector is formed by stacking all the obtained 2D probability maps for one volume. This output heatmap is coarser than the morphological filter output, but more robustly located around the vertebrae.

By combining the deep-learning vertebrae detector and the morphological filter responses, the network output is refined and the filter responses that are outside the spine are rejected, so that a robust spine binary mask is finally obtained for the abdominal image.

This is one way to identify the spine location, but any other suitable image processing techniques may be employed for detecting the unique spine shape.

The spine detection step of the torso segmentation basically involves identifying the spine, and using the center of mass of the spine binary mask to define the origin of a reference coordinate system. If the detected spine is highly curved, its center of mass might not belong to the binary mask. This is because the so-called barycenter of the spine can be outside the spine itself and hence not aligned with the mask. In this case, the binary mask point that is the closest to the center of mass is used. Then the extremities of the spine binary mask are used to define the vertical n-axis. Alternatively a normal direction tangential to the central point of the spine may be used.

By defining the n-axis, the image can be updated to include the n-axis information, for example by rotating the image to position the n-axis in the defined (e.g. vertical) orientation.

The second step in the segmentation of the abdominal image is to detect a second, orthogonal reference (orientation) axis. This is based on detection of the abdomen to define a transverse axis.

A set of planes are searched, each orthogonal to the first reference n-axis (or locally orthogonal to the spine). Searching for an orientation axis is conducted in a set of xy planes, each passing through a local origin, with the local origins as evenly spaced points along the spine.

Within each of these xy planes, abdomen detection takes place, for example using a variant of the Hough transform, tailored to the detection of circular or elliptical shapes. In practice, the best convolution of the image with a radially-symmetric kernel modeling a disk with the desired border profile is searched among a range of radii. A resulting convex hull of the abdomen, or segmented torso, is defined.

A method for performing the segmentation of the torso where the abdominal image only contains a partial view of the torso is described below with reference to FIG. 3.

The segmentation of the femur image may be performed using extremity classification based on a deep learning network, wherein the network is trained to identify and output coordinates of femur endpoints based on an input femur image. The deep learning network may include a dedicated machine learning algorithm trained to recognize the structure of a fetal femur in order to aid the segmentation of the femur image.

The segmentation may further comprise classifying the tissue surrounding the femur, such as muscle and fat, thereby generating a more accurate model of a leg of the fetus to be used in the final weight estimation. The classification of the surrounding tissues may be performed by any suitable segmentation method, such as intensity class separation (where the tissues are separated based on the local signal intensities) or with a dedicated machine learning algorithm.

In some case, the segmentation of the femur image may require a user input in order to correctly delineate the soft tissue boundaries. In this case, the segmentation of the femur image may be displayed for the user to monitor. The user may provide input to correct the segmentation of the femur image during the segmentation process or after the process has been completed. The user may provide an input through any suitable means, such as: indicating through a mouse click, or a tap on a touch screen, the correct location of a soft tissue boundary; or by drawing using a mouse, or touch screen, the correct soft tissue boundary. The user input, such as a boundary correction, may then be added to the data set used to train the machine learning algorithm used for tissue classification.

Further, it is possible to display the segmentations of each of the plurality of different three dimensional ultrasound images to a user in order to receive user input on the segmented images. Thus, the user may assess the segmentations before the method proceeds to the step of performing the fetal weight estimation, thereby ensuring the accuracy of the final estimation. An interactive tool to perform segmentation corrections may be provided as for each segmented image.

In step 170, the segmented images are used to perform a fetal weight estimation.

The fetal weight estimation may be performed using a global homogeneous tissue density. In other words, the densities of all the different tissues of the fetus may be averaged, thereby generating a unique density coefficient, and multiplied by the fetal volume discerned from the image segmentations in order to perform a fetal weight estimation with minimal computational cost. The average density of a fetus may be defined based on relevant literature.

Alternatively, the segmented images may undergo further processing in order to perform the fetal weight estimation, which is described below with reference to FIG. 4.

Figure 3:
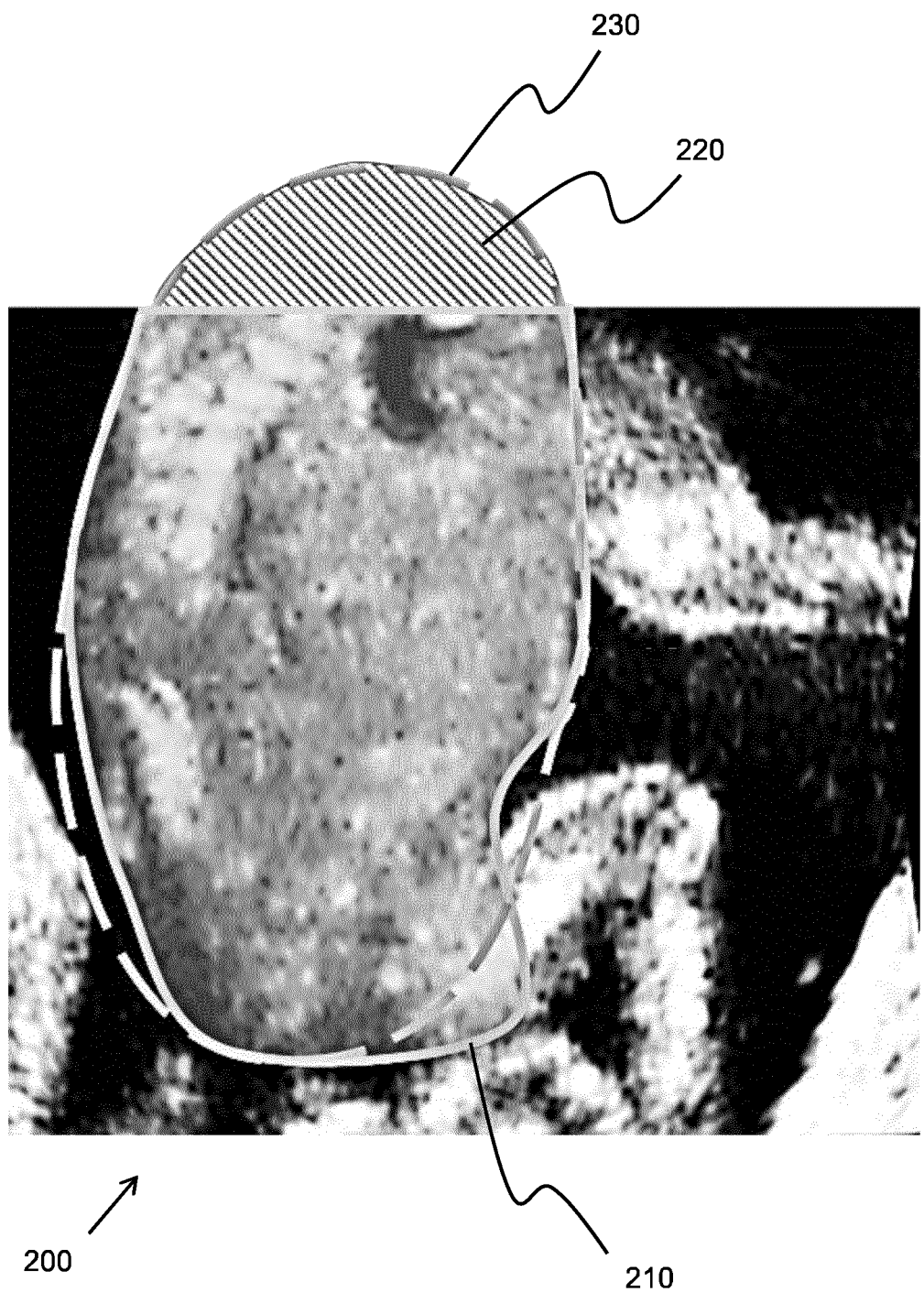
FIG. 3 shows a comparison between a conventional segmentation and a model fitting for an image with partial torso coverage.

FIG. 3 shows an abdominal image 200 comprising a partial view of the torso of the fetus. This partial imaging of the torso is a common problem in abdominal imaging cause by a limited field of view of the imaging probe.

Under normal segmentation operation, such as the method described above, the torso of the fetus is identified as indicated by the solid line outline 210; however, due to the partially incomplete view of the torso, the segmentation excludes the missing information 220, which would otherwise form the remaining portion of the torso of the fetus. This missing information would reduce the accuracy of the final fetal weight estimation.

The partial imaging of the torso may be compensated by way of a model torso image. The model torso image, in this case a model 230 with an ellipsoidal fitting, may be fit to the torso of the fetus based on the initial segmentation of the abdominal image. The model 230 and the segmented torso 210 may then be compared in order to obtain the ratio of the two volumes. Finally, the segmented torso is multiplied by the obtained ratio in order to compensate for the missing information.

The accuracy of the estimated fetal weight may be improved by identifying the volumes of the various tissues present within a segmented image.

Figure 4:
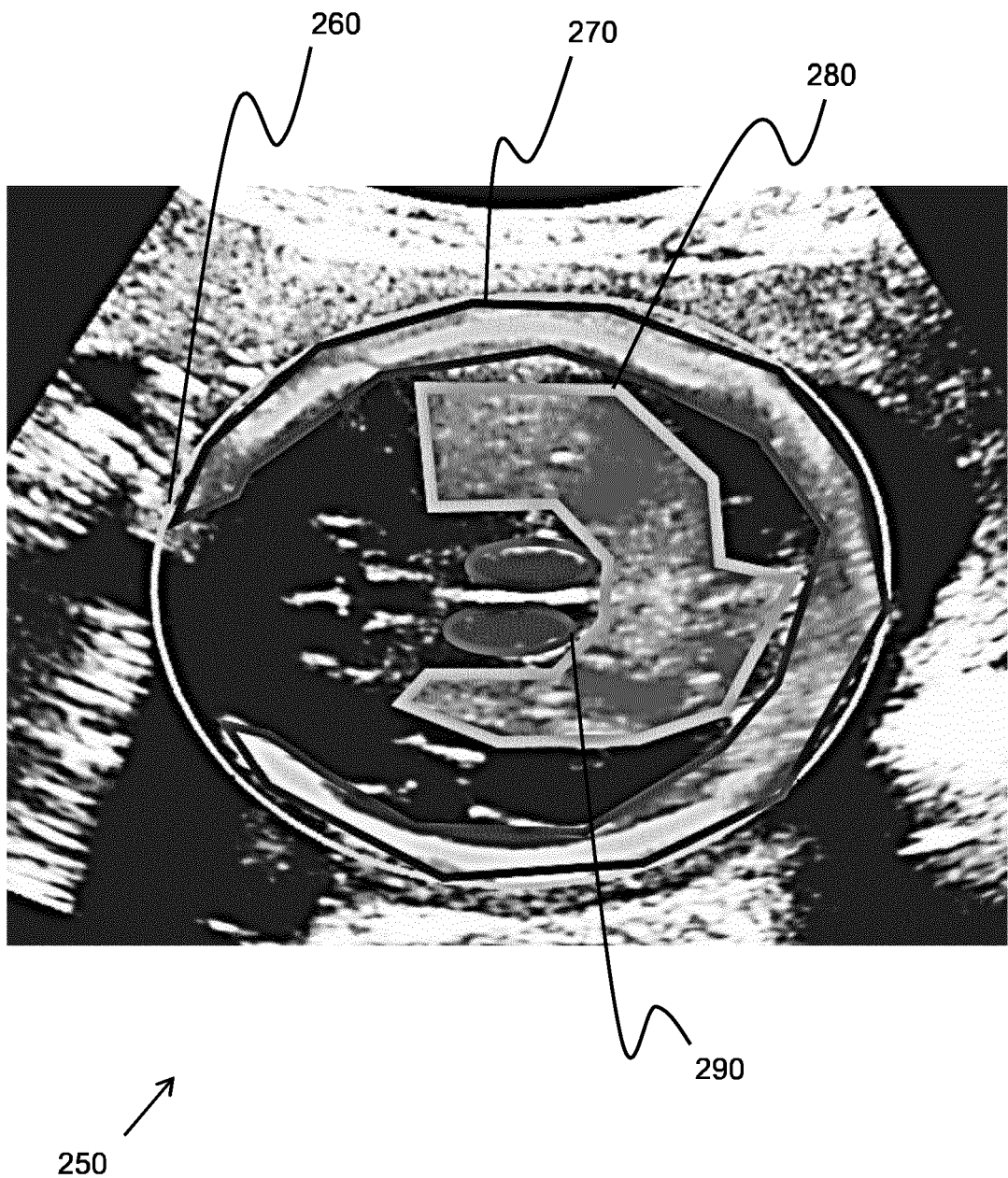
FIG. 4 shows a classification of tissue information within an image.

By way of example, FIG. 4 shows a head image 250 that has undergone tissue classification; however, the following method may also be applied to the abdominal, femur and humerus images.

The image shows a portion, also referred to as an internal volume, of the segmentation 260 of the head image. Within this internal volume, the signal intensities are analyzed and used to classify various tissue types present within the internal volume. Based on the tissue classification, it is possible to extract tissue information from the image. For example, within the internal volume shown in FIG. 4, there is: bone tissue 270, which corresponds to the skull of the fetus; soft tissue 280, which may correspond to the brain of the fetus; and fluid 290.

By performing this method across each segmented image, the tissue information of the entire imaged fetus may be combined and used in the fetal weight estimation. For example, the combined tissue information may specify the total volume of each tissue types, such as bone, present across all of the segmented images. Each combined tissue volume may then be multiplied by an associated tissue density coefficient, which is distinct for each tissue type in order to arrive at the fetal weight estimate.

Figure 5:
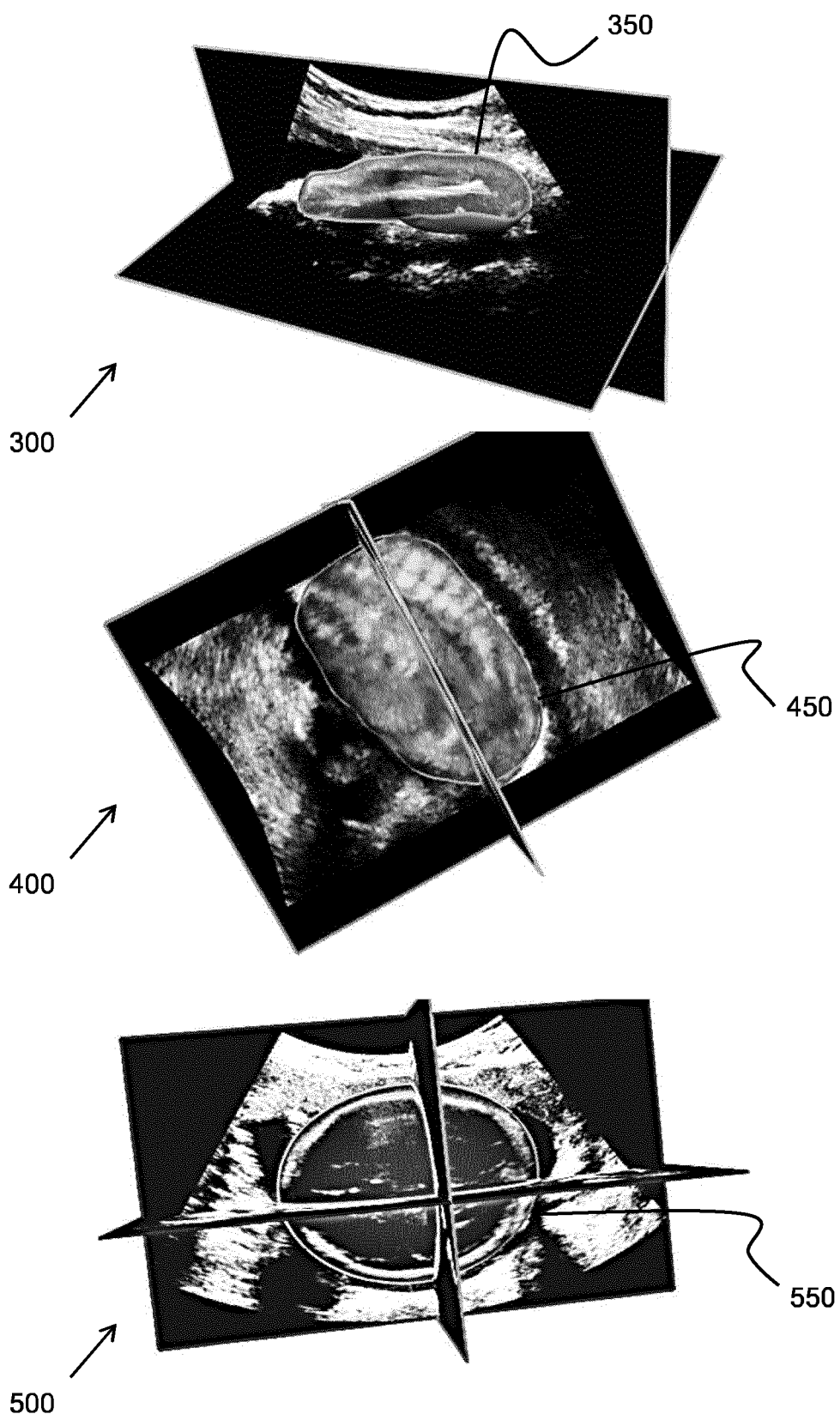
FIG. 5 shows the segmentations of the head, abdominal and femur images.

FIG. 5 shows: a femur image 300, including a leg segmentation 350; an abdominal image 400, including a torso segmentation 450; and a head image 500, including a skull segmentation 550.

This may be the form in which the segmented images are displayed to the user, wherein the user may manipulate the images in order to view them from a desired orientation. In this way, the user may provide input and/or corrections to every part of the segmented image in order to ensure the accuracy of the final fetal weight estimation.

Figure 6:
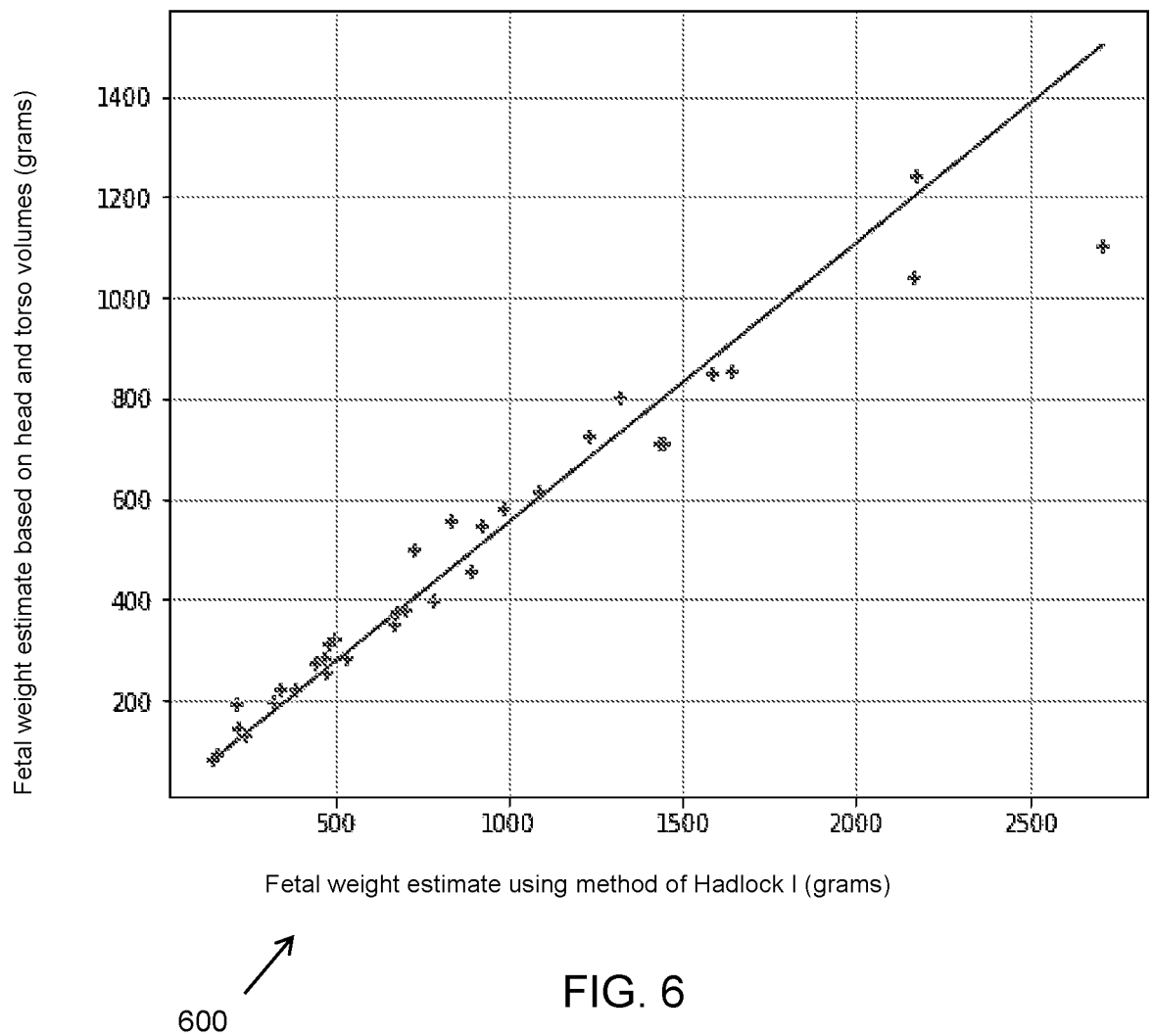
FIG. 6 shows a correlation between the proposed method and an existing estimation method.

FIG. 6 shows a plot 600 of the estimated fetal weight calculated using the methods described above (based on an abdominal and head image) against an existing fetal weight estimation method, known as Hadlock I, for a data set of 33 patients.

The resulting correlation coefficient is 0.91, with a slope of 0.55 and an intercept of −15 g. This strong correlation indicates the accuracy of the proposed method is at least as accurate as existing industry standards. In addition, the proposed approach may be combined with existing methods in order to complement the fetal weight estimates.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method for performing fetal weight estimation, the method comprising:
acquiring a plurality of different three dimensional ultrasound images of an imaging region, wherein the plurality of different three dimensional ultrasound images comprise:
a head image that includes a view of a head of a fetus;
an abdominal image that includes a view of a torso of the fetus; and
a femur image that includes a view of a leg of the fetus;
performing segmentation on each of the plurality of different three dimensional ultrasound images; and
performing the fetal weight estimation based on the segmentations of each of the plurality of different three dimensional ultrasound images; and wherein:
in response to a detection that the abdominal image comprises a partial view of the torso of the fetus, the segmentation of the abdominal image comprises:
generating a model torso image;
comparing the model torso image to the segmented abdominal image; and
calculating a volume ratio between the model torso image and the segmented abdominal image based on the comparison.

2. A method as claimed in claim 1, wherein the plurality of different three dimensional ultrasound images further comprises a humerus image.

3. A method as claimed in claim 1, wherein the segmentation of the femur image comprises:
detecting a femur by performing extremity classification based on a deep learning network; and
classifying tissue surrounding the femur.

4. A method as claimed in claim 3, wherein the classification of tissue surrounding the femur comprises segmenting the femur image based on a dedicated machine learning algorithm.

5. A method as claimed in claim 3, wherein the segmentation of the femur image comprises receiving user input.

6. A method as claimed in claim 1, wherein the method further comprises displaying the segmentations of each of the plurality of different three dimensional ultrasound images to a user.

7. A method as claimed in claim 6, wherein the method further comprises receiving user input based on the displayed segmentations.

8. A method as claimed in claim 1, wherein the fetal weight estimation is based on a global homogeneous tissue density.

9. A method as claimed in claim 1, wherein the fetal weight estimation comprises:
for each segmentation of the plurality of different three dimensional ultrasound images:
extracting an internal volume of the segmentation;
analyzing plurality of signal intensities within the internal volume;
classifying a plurality of tissue types within the internal volume based on the signal intensities; and
extracting tissue information based on the plurality of tissue types;
combining the tissue information extracted from each segmentation; and
estimating the fetal weight based on the tissue information.

10. A method as claimed in claim 9, wherein the plurality of tissue types comprises:
soft tissue;
bone; and
fluid.

11. A method as claimed in claim 9, wherein the tissue information comprises tissue volumes of the plurality of tissue types within the internal volume.

12. A method as claimed in claim 9, wherein the estimating of the fetal weight comprises:
applying an associated tissue density coefficient to each of the plurality of tissue types; and calculating a fetal weight estimate based on the tissue volumes and the associated tissue density coefficient of each of the plurality of tissue types.

13. An ultrasound imaging system comprising:
an ultrasound probe adapted to acquire a plurality of different three dimensional ultrasound images of an imaging region;
a display; and
a processor, wherein the processor is adapted to:
acquire the plurality of different three dimensional ultrasound images of the imaging region, wherein the plurality of different three dimensional ultrasound images comprise:
  a head image that includes a view of a head of a fetus;
  an abdominal image that includes a view of a torso of the fetus; and
  a femur image that includes a view of a leg of the fetus;
perform segmentation on each of the plurality of different three dimensional ultrasound images; and
perform fetal weight estimation based on the segmentations of each of the plurality of different three dimensional ultrasound images and wherein:
in response to a detection that the abdominal image comprises a partial view of the torso of the fetus, the segmentation of the abdominal image comprises:
generate a model torso image;
comparing the model torso image to the segmented abdominal image; and
calculating a volume ratio between the model torso image and the segmented abdominal image based on the comparison.

14. A non-transitory computer readable medium comprising computer program code which, in response to execution on a processor, to:
  acquire a plurality of different three dimensional ultrasound images of an imaging region, wherein the plurality of different three dimensional ultrasound images comprise:
    a head image that includes a view of a head of a fetus;
    an abdominal image that includes a view of a torso of the fetus; and
    a femur image that includes a view of a leg of the fetus;
  perform segmentation on each of the plurality of different three dimensional ultrasound images; and
  perform fetal weight estimation based on the segmentations of each of the plurality of different three dimensional ultrasound images; and wherein:
  in response to a detection that the abdominal image comprises a partial view of the torso of the fetus, the segmentation of the abdominal image comprises:
  generating a model torso image;
  comparing the model torso image to the segmented abdominal image; and
  calculating a volume ratio between the model torso image and the segmented abdominal image based on the comparison.

15. The non-transitory computer readable medium of claim 14, wherein the plurality of different three dimensional ultrasound images further comprises a humerus image.

16. The non-transitory computer readable medium of claim 14, wherein the segmentation of the femur image comprises: detecting a femur by performing extremity classification based on a deep learning network; and classifying tissue surrounding the femur.

17. The non-transitory computer readable medium of claim 16, wherein the classification of tissue surrounding the femur comprises segmenting the femur image based on a dedicated machine learning algorithm.

18. The non-transitory computer readable medium of claim 14, wherein the segmentation of the femur image comprises receiving user input.

19. The non-transitory computer readable medium of claim 14, further comprises displaying the segmentations of each of the plurality of different three dimensional ultrasound images to a user.

* * * * *